US008622902B2

(12) United States Patent
Woehrle

(10) Patent No.: US 8,622,902 B2
(45) Date of Patent: Jan. 7, 2014

(54) CONTROLLING AN ALARM IN A MEDICAL INSTRUMENT

(75) Inventor: Dieter Woehrle, Waiblingen (DE)

(73) Assignee: Koninklijke Philips N.V., Eindhoven (NL)

( * ) Notice: Subject to any disclaimer, the term of this patent is extended or adjusted under 35 U.S.C. 154(b) by 441 days.

(21) Appl. No.: 12/863,008

(22) PCT Filed: Jan. 19, 2009

(86) PCT No.: PCT/IB2009/050169
§ 371 (c)(1),
(2), (4) Date: Jul. 15, 2010

(87) PCT Pub. No.: WO2009/093159
PCT Pub. Date: Jul. 30, 2009

(65) Prior Publication Data
US 2010/0324377 A1 Dec. 23, 2010

(30) Foreign Application Priority Data

Jan. 21, 2008 (EP) .................................... 08100678

(51) Int. Cl.
*A61B 5/00* (2006.01)
*G06F 19/00* (2011.01)
(52) U.S. Cl.
CPC ................................. *G06F 19/3406* (2013.01)
USPC .......................................................... 600/301
(58) Field of Classification Search
USPC ................ 600/300–301; 340/539.12–539.14; 705/2–4
See application file for complete search history.

(56) References Cited

U.S. PATENT DOCUMENTS

| 5,368,026 | A | 11/1994 | Swedlow et al. |
| 5,438,983 | A | 8/1995 | Falcone |
| 5,865,736 | A | 2/1999 | Baker, Jr. et al. |
| 6,544,200 | B1 | 4/2003 | Smith et al. |
| 6,572,543 | B1 * | 6/2003 | Christopherson et al. ..... 600/300 |
| 6,725,074 | B1 | 4/2004 | Kastle |
| 6,996,427 | B2 | 2/2006 | Ali et al. |
| 7,123,950 | B2 | 10/2006 | Mannheimer |
| 7,590,465 | B2 * | 9/2009 | Higashide ...................... 700/109 |
| 7,629,890 | B2 * | 12/2009 | Sullivan et al. ............. 340/573.1 |
| 7,639,145 | B2 * | 12/2009 | Lawson et al. .............. 340/573.1 |
| 2002/0035315 | A1 * | 3/2002 | Ali et al. ........................ 600/300 |

(Continued)

FOREIGN PATENT DOCUMENTS

WO    03007815 A1    1/2003

*Primary Examiner* — Bill Thomson
*Assistant Examiner* — Bobby Soriano

(57) ABSTRACT

The invention concerns a method for controlling an alarm in a medical instrument or system, the medical instrument or system detecting at least one physiological parameter of the patient. The present value of the physiological parameter is consecutively detected and an alarm delay is determined as a function of at least one detected value of the physiological parameter wherein the function yields a shorter alarm delay for increasing values of the deviation from a normal value and a longer alarm delay for decreasing values of the deviation from the normal value. Further, the duration the value of the physiological parameter exceeds or under-runs at least one predefined threshold for the physiological parameter defining an upper or lower limit for a normal range of the physiological parameter, respectively, is measured and the alarm is generated when the duration the determined value of the physiological parameter exceeds or under-runs the predefined threshold exceeds the alarm delay. This method allows for the avoidance of nuisance alarms while still indicating severe conditions of the monitored patient reliably.

9 Claims, 3 Drawing Sheets

(56) References Cited

U.S. PATENT DOCUMENTS

| | | | |
|---|---|---|---|
| 2003/0018241 A1* | 1/2003 | Mannheimer | 600/300 |
| 2004/0073098 A1* | 4/2004 | Geva et al. | 600/300 |
| 2004/0236187 A1* | 11/2004 | Bock et al. | 600/300 |
| 2004/0249249 A1* | 12/2004 | Lawson et al. | 600/300 |
| 2007/0096927 A1* | 5/2007 | Albert | 340/573.1 |
| 2007/0156031 A1 | 7/2007 | Sullivan et al. | |
| 2007/0213599 A1* | 9/2007 | Siejko et al. | 600/300 |
| 2008/0071150 A1* | 3/2008 | Miesel et al. | 600/301 |
| 2008/0139898 A1* | 6/2008 | Johnson et al. | 600/301 |
| 2008/0169931 A1* | 7/2008 | Gentry et al. | 340/573.1 |
| 2008/0262322 A1* | 10/2008 | Gerber et al. | 600/301 |
| 2009/0043230 A1* | 2/2009 | Davis-Havill et al. | 600/595 |
| 2010/0016682 A1* | 1/2010 | Schluess et al. | 600/301 |

* cited by examiner

CONTROLLING AN ALARM IN A MEDICAL INSTRUMENT

FIELD OF THE INVENTION

The invention relates to the field of controlling an alarm in a medical instrument or system, the medical instrument or system detecting at least one physiological parameter of the patient.

BACKGROUND OF THE INVENTION

Typical patient monitoring systems and some other medical instruments and systems measure different physiological values, and, thus, can provide measurements of ECG, respiration, $SpO_2$, blood pressure etc. If a detected physiological parameter exceeds or under-runs a preset limit an alarm is generated.

However, in order to avoid nuisance alarms it is known to use an alarm delay between the event of exceeding or under-running a preset limit and the actual generation of the alarm. Such an alarm delay is often a compromise between warning the clinical staff fast enough about a change in the patient's condition on the one hand and generation of too many unjustified and, thus, nuisance alarms which detract the clinical staff from other work, especially more important alarms, on the other hand.

From U.S. Pat. No. 5,865,736 a method and apparatus for nuisance alarm reduction are known. There, it is described that when a detected value for a physiological parameter passes a threshold, both the amount of time in which the measured value has passed the threshold and the amount by which the threshold is passed are determined. Then a combination of the amount of time and of how much the measured value has passed the threshold, especially as an integral or some function of an integral, is calculated. An alarm is only generated, if the combination of the amount of time and of how much the measured value has passed the threshold exceeds a predefined threshold. However, with this method and apparatus nuisance alarms cannot be sufficiently avoided because the integral continues to increase as long as the measured physiological value is above the threshold, even if the amount of how much the threshold is passed is decreasing, i.e. the patient's condition is improving.

SUMMARY OF THE INVENTION

It is an object of the invention to provide such a method for controlling an alarm in a medical instrument or system and an according medical instrument or system that avoid generating nuisance alarms to a high degree.

According to the invention, this object is addressed by a method for controlling an alarm in a medical instrument or system, the medical instrument or system detecting at least one physiological parameter of the patient, the method comprising the following steps:

consecutively detecting the present value of the physiological parameter;

after detecting the present value of the physiological parameter, determining an alarm delay as a function of at least one detected value of the physiological parameter wherein the function yields a shorter alarm delay if the degree by which two consecutively determined values of the physiological parameter deviate from a normal value increases, and wherein the function yields a longer alarm delay if the degree by which two consecutively determined values of the physiological parameter deviate from the normal value decreases, measuring the time the physiological parameter has exceeded or under-run at least one predefined threshold for the physiological parameter defining an upper or lower limit for a normal range of the physiological parameter, respectively; and generating an alarm when the time the physiological parameter has exceeded or under-run the predefined threshold, respectively, exceeds the alarm delay.

Accordingly, it is an important idea of the invention to consider the present situation of the physiological parameter in order to determine the alarm delay in such a way that in case of decreasing abnormalities of the detected values a longer alarm delay is determined and vice versa. This means that a present alarm delay is extended if the patient's condition starts to improve again.

According to the invention, the degree by which two consecutively determined values of the physiological parameter deviate from a normal value is considered. This normal value can be one single value or some value of a range of values.

Since the alarm delay is determined as a function of at least one detected value of the physiological parameter, a formula or a look-up table comprising this parameter can be used. Further, in general, the present value of the physiological parameter can be detected in time intervals of varying duration. However, it is preferred to detect the present value of the physiological parameter with a predefined frequency, i.e. in time intervals of equal durations. According to a preferred embodiment of the invention, the alarm delay can be determined either from the absolute or relative amounts the physiological parameter deviates from the normal value.

Further, according to a preferred embodiment of the invention, the function for determining the alarm delay considers the degree by which the present value exceeds or under-runs at least one predefined threshold defining an upper or lower limit for a normal range of the physiological parameter, respectively, and the function yields a longer alarm delay for a lesser degree of exceeding or under-running the predefined threshold, respectively, and vice versa. Accordingly, the more the present value exceeds or under-runs the predefined threshold the earlier an alarm is generated in order to warn the clinical staff about a change in the patient's condition.

Generally, it is possible that the function of at least one detected value of the physiological parameter allows for very short and very long alarm delays. However, according to a preferred embodiment of the invention, a maximum alarm delay and/or a minimum alarm delay are defined. Especially when the function is defined by a mathematical formula, this way it can be avoided to generate very long alarm delays in case the present value of the physiological parameter deviates from the normal value by only a small amount.

The start of the alarm delay, i.e. the event that triggers a limit violation counter to run, can be defined in different ways. However, according to a preferred embodiment of the invention, the limit violation counter starts running after the first of multiple directly consecutive events of detected present values of the physiological parameter that exceed or under-run the threshold, respectively.

Generally, it is possible to keep the alarm delay fixed. However, according to a preferred embodiment of the invention, the value of the alarm delay is continuously updated according to a function of at least one detected value of the physiological parameter. This means that, according to this preferred embodiment of the invention, the limit violation counter starts running when the detected value of the physiological parameter exceeds or under-runs the predefined threshold for the first time, wherein the alarm delay changes according to a change of the detected value of the physiological parameter.

Accordingly, if the detected value of the physiological parameter exceeds the predefined threshold and increases further, the value for the alarm delay which is calculated from the first event of exceeding the threshold is getting shorter and shorter until the limit violation counter exceeds the alarm delay and the alarm is actually generated. However, there might be cases in which due to a decreasing value of the detected physiological parameter after exceeding the threshold the determined alarm delay gets longer and longer, and finally before the limit violation counter has exceeded the alarm delay, the value crosses the threshold and reenters the normal range of the physiological parameter. In this case no alarm is generated.

When the detected value of the physiological parameter has returned into the normal range, in general, the alarm condition and limit violation counter can be "reset" which means that the fact that the threshold has been exceeded or under-run at least once is not considered for future alarm generation. However, according to a preferred embodiment of the invention, the duration of the limit violation is determined when the detected present value of the physiological parameter has returned into the normal range, a reduction value is calculated as a function of the duration of the limit violation and/or the amount by which the limit was violated, and the reduction value is decremented in time. This method according to a preferred embodiment of the invention provides for different further measures:

According to a further preferred embodiment of the invention, a subsequently running alarm delay is reduced by the present reduction value. This means that the limit violation counter does not start from zero if another exceeding or under-running of the threshold has occurred shortly before. This way, severe and deteriorating conditions of the patient can be indicated by an alarm reliably and with short delay.

With respect to the event that resets the alarm condition, according to a preferred embodiment of the invention, it is possible that the alarm condition is cleared when the detected present value of the physiological parameter has returned into the normal range. According to this embodiment of the invention no severe condition of the patient is assumed as soon as the value of the physiological parameter is back in normal range.

However, according to an alternative preferred embodiment of the invention, the alarm condition is only cleared when the above described reduction value has reached zero. This means that the alarm condition remains active after the physiological parameter has returned into the normal range, and only clears when the reduction value which is decremented in time has reached zero. This way, in case of multiple short alarm events closely succeeding one another, these alarm events are practically "merged" into one alarm condition of longer duration.

Above mentioned object of the invention is further adressed by a medical instrument or system for detecting a physiological parameter and controlling an alarm, comprising a detector for consecutively detecting the present value of at least one physiological parameter of the patient;

a determination unit for determining an alarm delay as a function of at least one detected value of the physiological parameter, wherein the function yields a shorter alarm delay if the degree by which two consecutively determined values of the physiological parameter deviate from a normal value increases, and wherein the function yields a longer alarm delay if the degree by which two consecutively determined values of the physiological parameter deviate from the normal value decreases, a timer for counting the time the physiological parameter has exceeded or under-run at least one predefined threshold for the physiological parameter defining an upper or lower limit for a normal range of the physiological parameter, respectively; and an alarm unit for generating the alarm when the time the physiological parameter has exceeded or under-run the predefined threshold, respectively, exceeds the alarm delay.

This medical instrument or system is preferably operated according to one or more of the methods described above.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

According to a first embodiment of the invention the alarm delay is calculated by the following formula:

$$A(nT)=\text{abs}(L/(V(nT)-L))*D_{x\%}*X\%/100\% \qquad (1),$$

wherein:

$A(nT)$=alarm delay at nT

T=update period

L=normal value or upper or lower limit of a normal range $V(nT)$=value of the physiological parameter at nT $D_{x\%}$=selected alarm delay at X % exceeding of the alarm limit (L).

Figure 1:
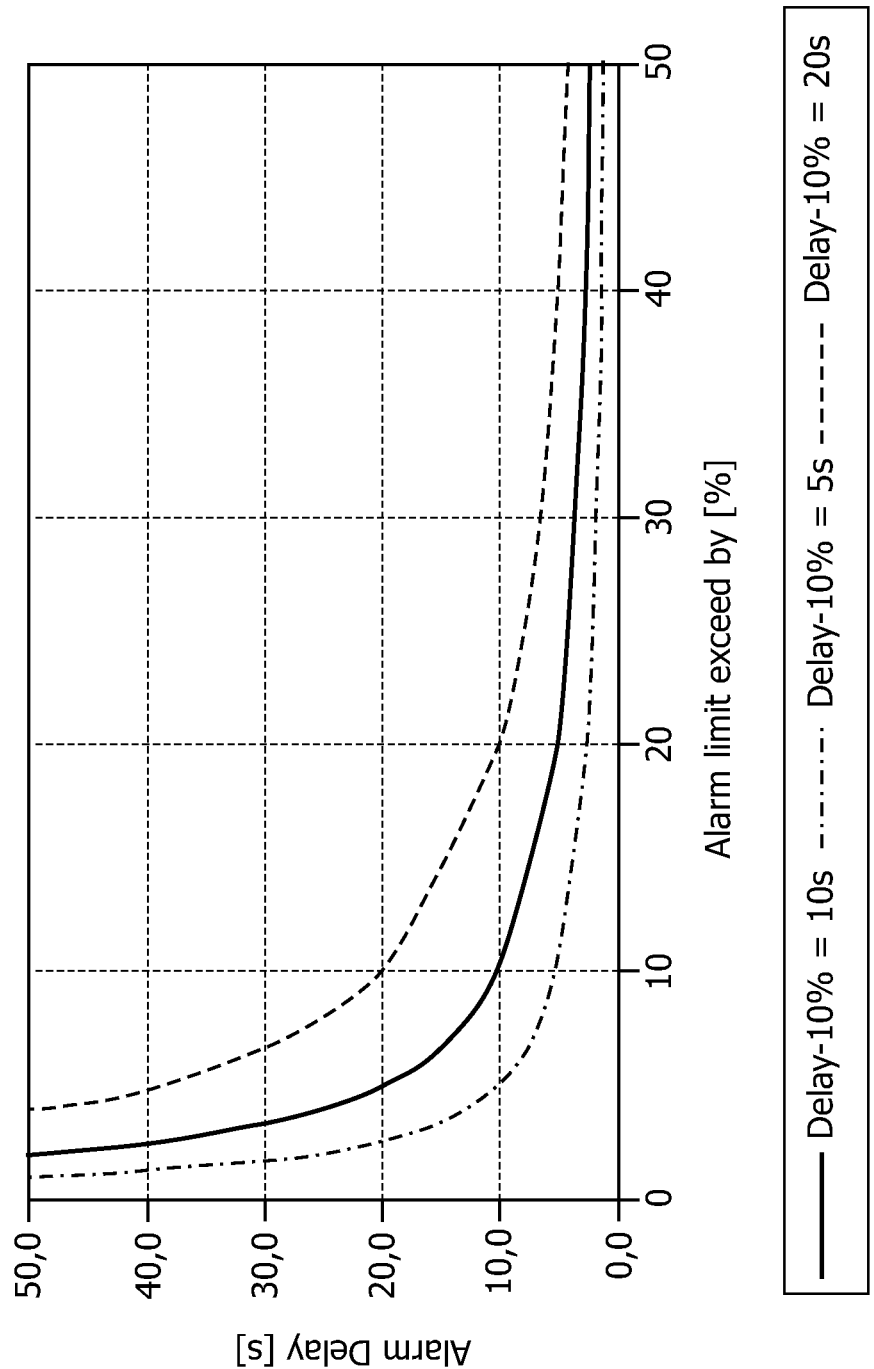
FIG. 1 shows graphs of alarm delay curves according to a first preferred embodiment of the invention.

Graphs of the according curves of the alarm delay versus the percentage by which the normal value or limit is exceeded are shown in FIG. 1. As can be seen from FIG. 1, small percentages cause high alarm delays according to formula (1). Accordingly, in order to avoid too long delays, the alarm delay calculated according to formula (1) can be limited by a minimum value and/or a maximum value. A minimum alarm delay is beneficial to prevent nuisance alarms resulting from brief changes of the physiological value which might be caused by artifacts. Further, a maximum alarm delay ensures that an alarm is generated after a predefined maximum delay even in cases where the physiological value exceeds the limit by only a small amount.

According to a second embodiment of the invention, the following formula can be used to calculate the alarm delay:

$$A(nT)=D_{max}-S*\text{abs}(V(nT)-L)/L \qquad (2),$$

wherein:

$A(nT)$=alarm delay at nT

T=update period

L=normal value or upper or lower limit of a normal range $V(nT)$=value of the physiological parameter at nT $D_{max}$=maximum alarm delay S=slope with which the alarm delay decreases if the amount by which the physiological value exceeds the alarm limit increases.

Figure 2:
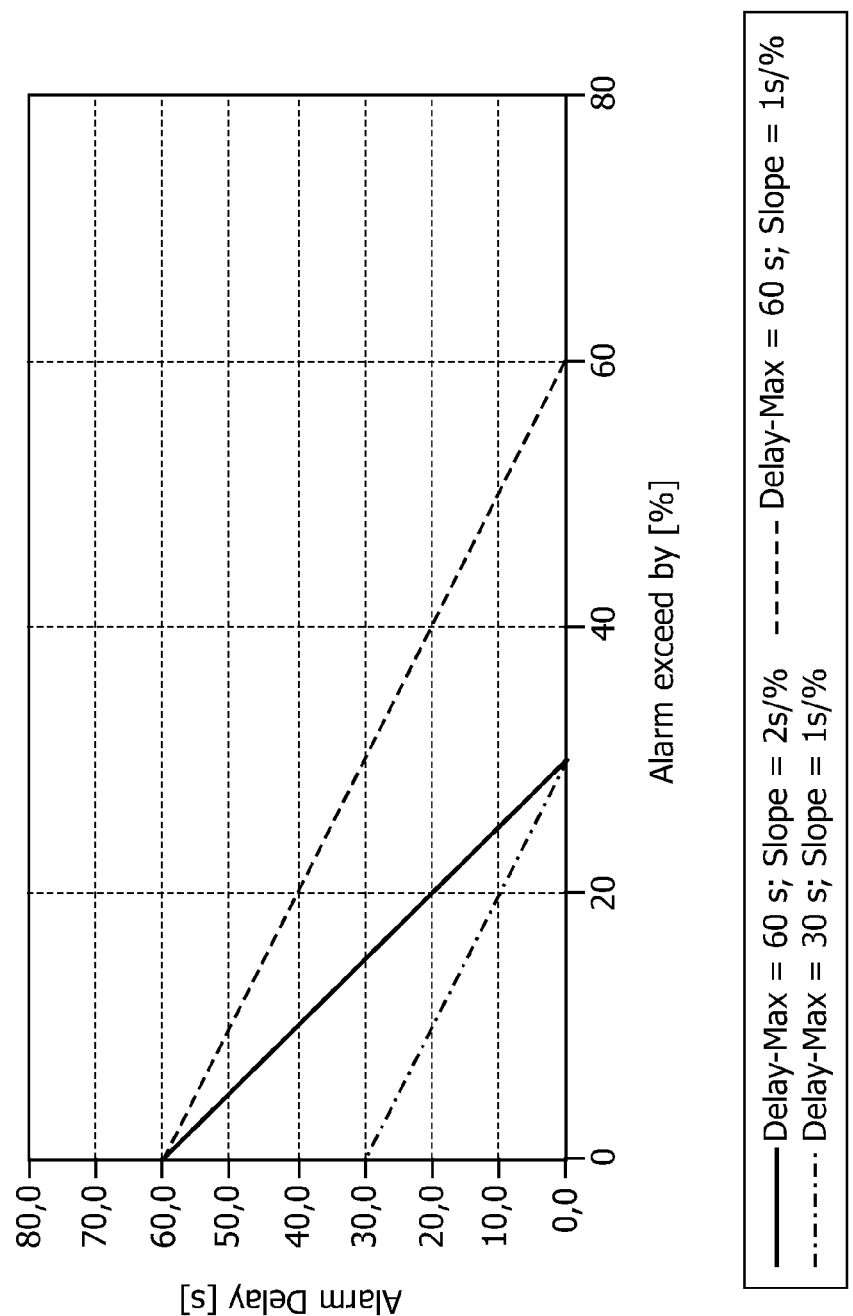
FIG. 2 shows graphs of alarm delay curves according to a second preferred embodiment of the invention.

This formula does not only consider the amount by which the physiological value exceeds the limit but also takes also into consideration the slope with which the alarm delay decreases if the amount by which the physiological value exceeds the alarm limit increases. The graph of according curves can be seen from FIG. 2. An offset may be added to formula (2) to get a minimum alarm delay.

Figure 3:
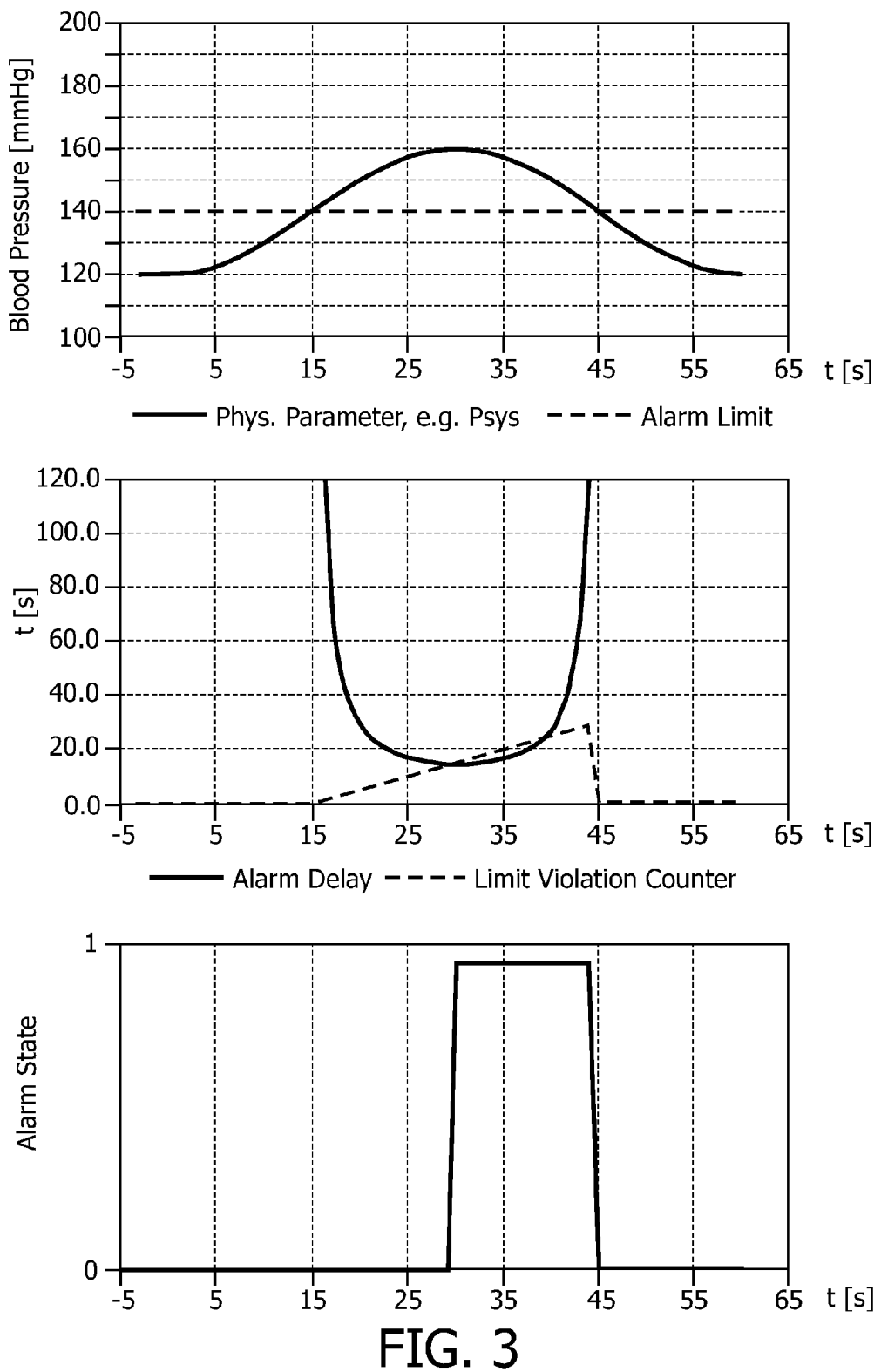
FIG. 3 shows an example for generating an alarm according to the first preferred embodiment of the invention.

From FIG. 3 an example for generating an alarm according to the first preferred embodiment of the invention can be seen. The upper graph shows the blood pressure as the physiological value and an according alarm limit. At t=15 s the blood pressure reaches the alarm limit and the limit violation counter starts to run as shown in the graph in the middle. There, the alarm delay calculated according to a formula similar to formula (1) is shown, too. With exceeding blood pressure the alarm delay becomes smaller and smaller. At t=29 s the value of the limit violation counter exceeds the alarm delay and, thus, as can be seen from the graph at the bottom, the alarm state changes from 0 to 1 which means that an alarm is generated. When the blood pressure starts to decrease, the alarm delay increases again. Finally, at t=45 s the decreasing blood pressure reaches the alarm limit again and, thus, the alarm state changes from 1 to 0 which means that the alarm is stopped. Further, the limit violation counter is reset, too.

According to a third embodiment of the invention, as shown below, a look-up table for the alarm delay is used instead of a formula:

| relative amount by which the limit is exceeded | resulting alarm delay |
|---|---|
| <10% | 60 s |
| 10 to 20% | 20 s |
| 20 to 30% | 12 s |
| 30 to 40% | 9 s |
| 40 to 50% | 7 s |
| >50% | 5 s |

Further, instead of making the alarm delay dependent on the absolute or relative amount by which the limit is exceeded or under-run, the alarm delay can be made dependent on the absolute value of the physiological parameter, the relative or absolute deviation of the physiological parameter from a normal value or the relative or absolute deviation from any predefined values.

For measuring the time since the physiological parameter has exceeded the upper limit or has under-run the lower limit, the limit violation timer is started as soon as the physiological value has crossed the according limit, respectively. At each time interval T the current alarm delay is calculated based on the current value of the physiological parameter and the resulting alarm delay is then compared with the current value of the limit violation timer. If the value of the limit violation timer exceeds the current alarm delay, an alarm is generated. As soon as the physiological value has returned into the normal range between the upper limit and the lower limit, the alarm condition and limit violation timer can be cleared.

However, according to an alternative embodiment of the invention, the alarm condition is cleared and the limit violation is decremented at intervals of T by a recovery factor was soon as the physiological value has returned into the normal range. This has the advantage that the limit violation counter does not start from zero and the actual alarm delay is shorter if the physiological parameter exceeds or under-runs the limit repetitively within a short period of time. Thus, for this embodiment it is less likely that repetitive short events remain undetected.

According to a further embodiment of the invention, the limit violation counter is decremented at intervals of T by a recovery factor of was soon as the physiological value has returned into the normal range, and the alarm condition is reset as soon as the limit violation counter reaches zero. This has the advantage that, if there are multiple short alarm events closely succeeding one another, these multiple alarm conditions are merged into one common alarm condition of longer duration.

According to the two latter embodiments of the invention, the limit violation counter may be set to a predetermined value and then decremented at intervals of T by a recovery factor of was soon as the physiological value has returned into the normal range. Further, the value of the limit violation counter may be calculated as a function of the duration of the limit violation and/or the absolute or relative amount by which the physiological parameter has exceeded or under-run the limit, the relative or absolute amount by which the physiological parameter has deviated from a normal value or the relative or absolute amount by which the physiological parameter has deviated from any predetermined value.

As a result, a medical instrument or system and method are provided that allow for avoidance of nuisance alarms while still detecting severe conditions of a patient reliably and with short delay.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A method for controlling an alarm unit in a medical instrument or system, the medical instrument or system detecting at least one physiological parameter of the patient, the method comprising:

with the medical instrument or system, consecutively detecting a present value of the physiological parameter;

with a determination unit, after detecting the present value of the physiological parameter, determining an alarm delay as a function of at least one detected value of the physiological parameter wherein the function yields a shorter alarm delay if the degree by which two consecutively determined values of the physiological parameter deviate from a normal value increases, and wherein the function yields a longer alarm delay if the degree by which two consecutively determined values of the physiological parameter deviate from the normal value decreases;

measuring a time the physiological parameter has exceeded or under-run at least one predefined threshold for the physiological parameter defining an upper or lower limit for a normal range of the physiological parameter, respectively;

starting a limit violation counter running after a first of multiple directly consecutive events of detected present values of the physiological parameter that exceed or under-run the threshold, respectively, and wherein the value of the alarm delay is continuously updated according to the function of at least the detected value of the physiological parameter;

determining the value of the limit violation counter when a detected present value of the physiological parameter has returned into a normal range, a reduction value is calculated as a function of the detected present value of the limit violation counter and/or the degree by which the detected present value of the physiological parameter exceeds or under-runs the predefined threshold, and the reduction value is decremented in time; and controlling the alarm unit to generate an alarm when the time of the physiological parameter exceeds or under-runs the predefined threshold, respectively, exceeds the alarm delay.

2. The method according to claim 1, wherein the most recently detected value of the physiological parameter is used for determining the alarm delay.

3. The method according to claim 1, wherein the determination unit considers the degree by which the detected value exceeds or under-runs the predefined threshold, respectively, and wherein the function yields a longer alarm delay for a lesser degree of exceeding or under-running the predefined threshold, respectively, and vice versa.

4. The method according to claim 1, wherein a maximum alarm delay and/or a minimum alarm delay are defined.

5. The method according to claim 1, wherein the reduction value is equal to the value of the limit violation counter when the detected present value of the physiological parameter has returned into the normal range.

6. The method according to claim 1, wherein a subsequently alarm delay is reduced by the present reduction value.

7. The method according to claim 1, wherein the alarm condition is only cleared when the reduction value has reached zero.

8. The method according to claim 1, wherein the alarm condition is cleared when the detected present value of the physiological parameter has returned into the normal range.

9. A medical instrument or system for detecting a physiological parameter and controlling an alarm, comprising a detector for consecutively detecting the present value of at least one physiological parameter of the patient;

a determination unit for determining an alarm delay as a function of at least one detected value of the physiological parameter, wherein the function yields a shorter alarm delay if the degree by which two consecutively determined values of the physiological parameter deviate from a normal value increases, and wherein the function yields a longer alarm delay if the degree by which two consecutively determined values of the physiological parameter deviate from the normal value decreases, a timer for counting the time the physiological parameter has exceeded or under-run at least one predefined threshold for the physiological parameter defining an upper or lower limit for a normal range of the physiological parameter, respectively; and an alarm unit for generating the alarm when the time the physiological parameter has exceeded or under-run the predefined threshold, respectively, exceeds the alarm delay, wherein a limit violation counter starts running after the first of multiple directly consecutive events of detected present values of the physiological parameter that exceed or under-run the threshold, respectively, and wherein the value of the alarm delay is continuously updated according to a function of at least the detected value of the physiological parameter; and wherein the value of the limit violation counter is determined when the detected present value of the of the physiological parameter has returned into the normal range, a reduction value is calculated as a function of the value of the limit violation counter and/or the degree by which the detected value of the physiological parameter has exceeded or under-run the predefined threshold, and the reduction value is decremented in time.

* * * * *